United States Patent [19]
Cima

[11] 4,424,598
[45] Jan. 10, 1984

[54] MULTI-MODE BATH MODULE

[75] Inventor: Louis E. Cima, Adamsville, Tenn.

[73] Assignee: Aqua Glass Corporation, Adamsville, Tenn.

[21] Appl. No.: 399,795

[22] Filed: Jul. 19, 1982

[51] Int. Cl.³ .......................................... A61H 33/06
[52] U.S. Cl. ......................................... 4/524; 4/546; 4/541; 4/559; 4/597; 4/605; 4/612
[58] Field of Search .................. 4/524, 525, 533, 535, 4/538, 541–544, 546, 557, 559, 567, 568, 571/573, 576, 584, 596, 597, 598, 601–603, 605, 607, 611–615, 661, 192; 128/66; 52/34, 35

[56] References Cited
U.S. PATENT DOCUMENTS

| D. 186,841 | 12/1959 | Everett | 4/596 X |
|---|---|---|---|
| 3,007,178 | 11/1961 | Altman et al. | 4/525 |
| 3,479,778 | 11/1969 | Johnson | 4/538 |
| 3,884,258 | 5/1975 | Mull | 4/615 |
| 4,153,954 | 5/1979 | Jacuzzi et al. | 4/544 |
| 4,237,562 | 12/1980 | Dupont | 4/543 |
| 4,340,981 | 7/1982 | Vanags | 4/524 |

*Primary Examiner*—Stephen Marcus
*Assistant Examiner*—Kenneth S. Putnam

[57] ABSTRACT

Bath module includes a shell-like housing defining interiorly a tub/shower facility wherein whirlpool, steam, tanning and mist functions or modes of operation are selectable through actuation of pneumatic controls located therein. The preferred embodiment includes recessed storage and grab bar compartments, the recessed storage compartment housing the pneumatic controls as well as other items.

6 Claims, 7 Drawing Figures

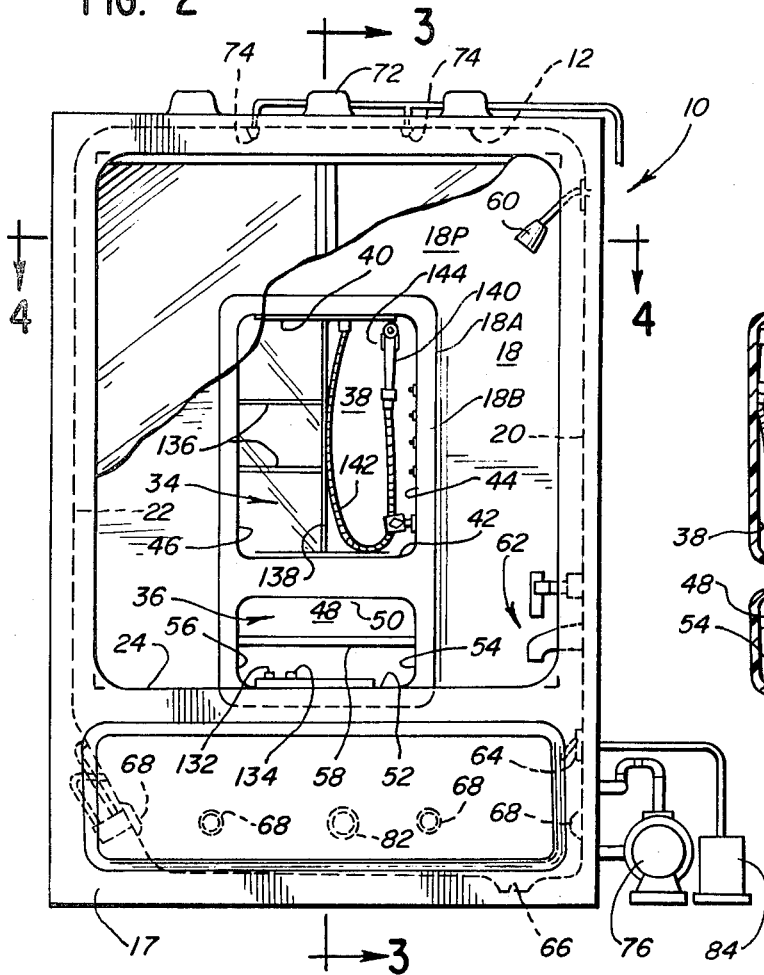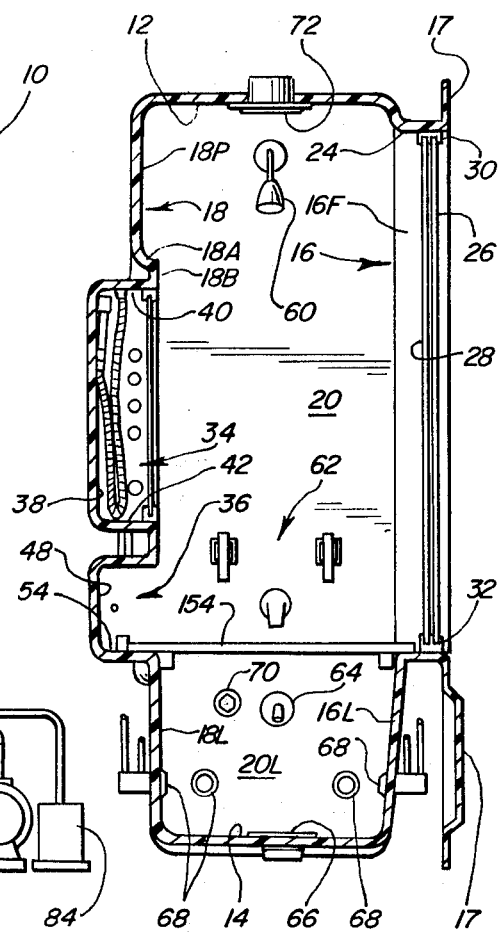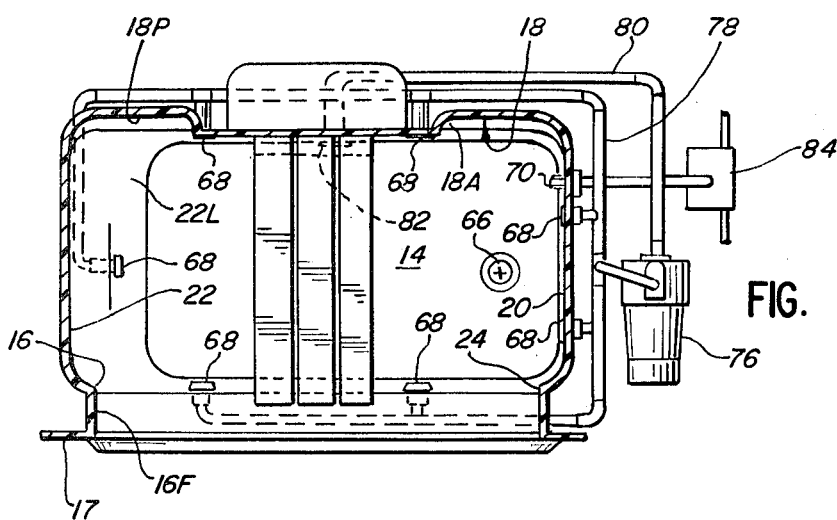
FIG. 2
FIG. 3
FIG. 4

MULTI-MODE BATH MODULE

The present invention relates generally to shower/tub constructions and, more particularly to self-contained bathing or shower installations. Specifically, the present invention concerns a novel multi-mode bath module providing a variety of modes of operation including whirlpool, steam, mist and tanning modes in addition to normal bath and shower.

A variety of integrated systems are commercially available which generally afford the foregoing modes of operation. Prior to the present invention, however, the available systems purposefully required the user (for safety reasons) to select the mode of modes of operation at a control station located remote from the interior (i.e., shower/bath stall). Such is, of course, somewhat inconvenient to a user after already entering and getting wet.

Commercially available systems capable of affording the foregoing functions or modes of operation are also expensive to install, requiring substantial general construction, plumbing and electrical work.

SUMMARY OF THE INVENTION

An object of the present invention is to provide multi-mode bath module which is easy to install, relatively inexpensive and extremely convenient in use for the user.

A more specific object of the invention is to provide a means of permitting the user to safely control the modes of operation or functioning of the bath module without leaving the interior thereof, even when the user is sitting or standing in water.

A further object is to provide enhanced safety and convenience to the user through provision of readily accessible, but non-protruding, storage and grab bar facility within the station.

In accordance with the invention a multi-mode bath module comprises spaced apart top and bottom walls with opposed pairs of side and end walls extending generally vertically therebetween to jointly therewith define the interior of the module. The walls are joined integrally to define a unitary shell-like structure. One of the side walls has a relatively large opening to provide user access to the interior. Suitable doors, preferably sliding doors, are mounted to open and close the access. The walls also have a plurality of relatively small openings in which are mounted the mode determining inputs, such as an ultra-violet lamp for tanning, mist heads, nozzles for whirlpool and steam heads. Connected to the inputs are facilities for enabling operation thereof. Such facilities include delivery systems including the electrical lines (for the lamp), a steam generator, whirlpool pump and related plumbing. Such facilities further include operating systems for the delivery systems. The operating systems are of the electro-pneumatic type wherein electric switching is responsive to pneumatic control signals. Controls for producing the pneumatic control signals are located within the station interior for the user so that electrical switching can be safely accomplished through the expedient of pneumatic control.

In the presently preferred form illustrated herein the pneumatic controls are located within a recessed portion of one of the vertical walls, preferably the side wall opposite that of the access opening.

Recessed storage and grab bar compartments are also provided in the illustrated embodiment to enhance convenience and safety.

The illustrated embodiment advantageously locates the pneumatic controls in the recessed storage compartment, the storage compartment having shelves for supporting vanity items and a sliding door to prevent the vanity items from accidentally falling out.

Another feature of the preferred embodiment relates to the convenient and safe housing of a hand held shower unit within the same recessed storage compartment which houses the pneumatic controls and vanity shelves. The shelves extend less than full length of the compartment to afford room for the pneumatic controls and hand held shower unit.

The lower portions of the vertical walls together with the bottom wall define a tub for regular bathing and for the whirlpool, the recessed grab bar compartment being formed in the vertical side wall opposite the access immediately above the lower tub defining portion thereof and the recessed storage compartment being formed in the same wall immediately above the grab bar compartment.

Further enhancing safety and convenience, air volume controls for controlling the intensity of the whirlpool jet inputs are disposed in a recessed location at the base of the grab bar recess compartment.

With the foregoing general arrangement the user is isolated from protrusions within the station other than the standard fixed shower head and faucet fixtures.

Other features and advantages of the invention will be apparent from the following description and claims and are illustrated in the accompanying drawings which show structure embodying preferred features of the present invention and the principles thereof, and what is now considered to be the best mode in which to apply these principles.

BRIEF DESCRIPTION OF THE DRAWINGS

In the accompanying drawings forming a part of the specification, and in which like numerals are employed to designate like parts throughout the same:

FIG. 2 is a front elevational view of the module of FIG. 1;

FIG. 3 is a sectional view taken, as indicated, along the line 3—3 of FIG. 2;

FIG. 4 is a sectional view taken, as indicated, along the line 4—4 of FIG. 3;

DETAILED DESCRIPTION

Figure 1:
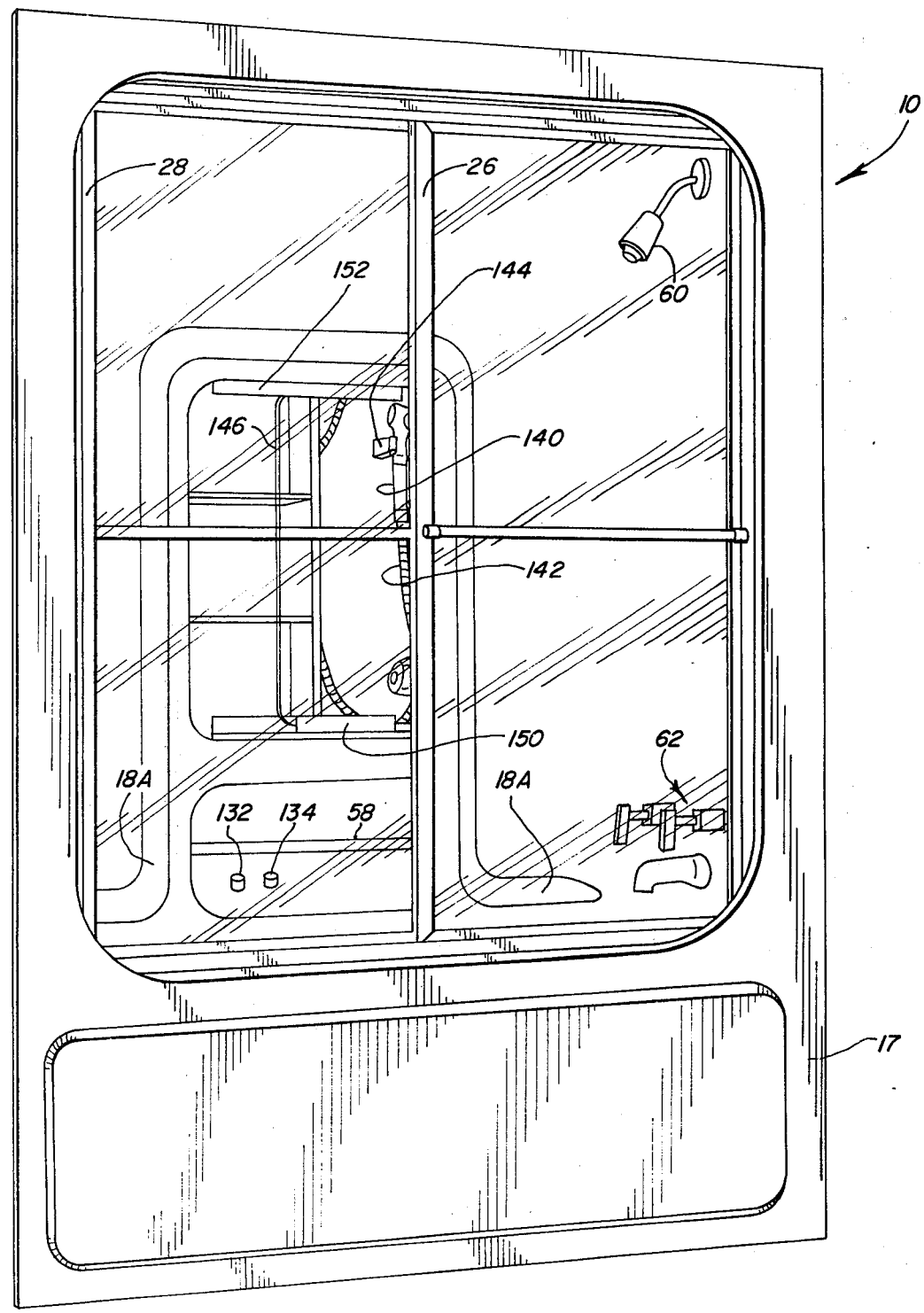
FIG. 1 is a perspective view showing the front and portions of the interior of a multi-mode bath module in accordance with the present invention as installed in a user's bathroom.

Referring now to the drawings, a multi-mode bath module 10 in accordance with the invention is shown in its presently preferred form comprising a hollow, shell-like structure that includes spaced apart top and bottom walls 12, 14 with opposed pairs of side walls 16, 18 and end walls 20, 22 extending generally vertically there between to jointly therewith define the interior of the module. The walls 12, 14, 16, 18, 20 and 22 are joined integrally to thereby define a monolithic shell-like structure. Preferably, the walls are formed via a vacuum forming process of a thermal plastic material such as acrylic.

The lower portions 16L, 18L of side walls 16, 18 and the lower portions 20L, 22L of end walls 20, 22 together with the bottom wall 14 define a tub like structure suitable for bathing and/or whirlpool as will be described hereinafter.

The upper portion of the side wall 16 has a relatively large opening 24 to provide user access to the interior, the opening being surrounded by an outwardly flared portion 16F of wall 16 which, in turn, integrally merges with a frontal facing wall 17. Sliding doors 26, 28 are guided by tracks 30, 32 mounted along the upper and lower surfaces of flared portion 16F to open and close the access.

The upper portion of the other side wall 18 includes a planar region 18P which is offset outwardly (viewed from the interior) from the lower tub defining portion 18L thereof via a sloping portion 18A.

Recessed storage and grab bar compartments 34, 36 are formed in the upper portion of side wall 18. The recessed storage compartment 34 includes a vertical back wall portion 38 offset outwardly (when viewed from the interior) from the planar region 18P. Upper, lower and a part of opposed end wall portions 40, 42, 44 and 46, respectively, extend transversely inwardly from the back wall portion 38 a distance beyond the planar region 18P and terminate substantially in a plane that is substantially complanar of the lower portion 18L of side wall 18. The recessed grab bar compartment 36 includes a back wall portion 48 similarly offset from planar region 18P and similar upper, lower and end wall portions 50, 52, 54 and 56, respectively. A grab bar 58 is suitably mounted to extend between end wall portions 54 and 56, as shown.

The sloping portions 18A and a merging border 18B encircle compartments 34, 36 in picture frame like fashion.

End wall 20 includes a plurality of relatively small openings or ports (not shown) to accommodate a standard fixed shower head 60, and valve and faucet assembly 62. A conventional mechanical drain lever 64 is mounted in conventional fashion to open and close a water drain 66 provided in the bottom wall 14.

As noted above, the multi-mode bath module 10 affords whirlpool, steam, tanning and mist functions in addition to standard bath and shower. To this end, mode determining inputs are provided. In the case of the whirlpool mode, the inputs comprise a plurality of standard water jet nozzels 68 mounted through appropriate ports or openings in the lower portions 16L, 18L, 20L and 22L of walls 16, 18, 20 and 22, there being two nozzels 68 located along portions 16L, 18L and 20L and a single nozzel located along wall portion 22L. In the case of the steam mode or function the input comprises a standard steam head 70 mounted through a suitable port located along wall portion 20L. The mode determining input in the case of the tanning mode comprises an ultraviolet lamp 72 mounted through an appropriate opening in the top wall 12. Finally, in the case of mist the mode determining inputs comprise a pair of standard mist or rain heads 74 also mounted through suitable openings in the top wall 12.

Facilities for enabling operation of the mode determining inputs 68, 70, 72 and 74 comprise delivery and operating systems. As will be described, such facilities permit the user to safely select and vary the modes of operation without leaving the interior of the module.

The delivery system for the whirlpool mode includes a pump 76, and plumbing comprising water pipe line 78 for delivering water under pressure to the whirlpool jets 68 and a water pipe line 80 for returning water to pump 76. As shown, water pipe line 80 is connected to a strainer 82 mounted in an opening of the lower portion 10L of wall 18.

The delivery system for the steam mode includes a steam generator 84 and steam line 86 connected between the generator 84 and the steam head 70.

Figure 5:
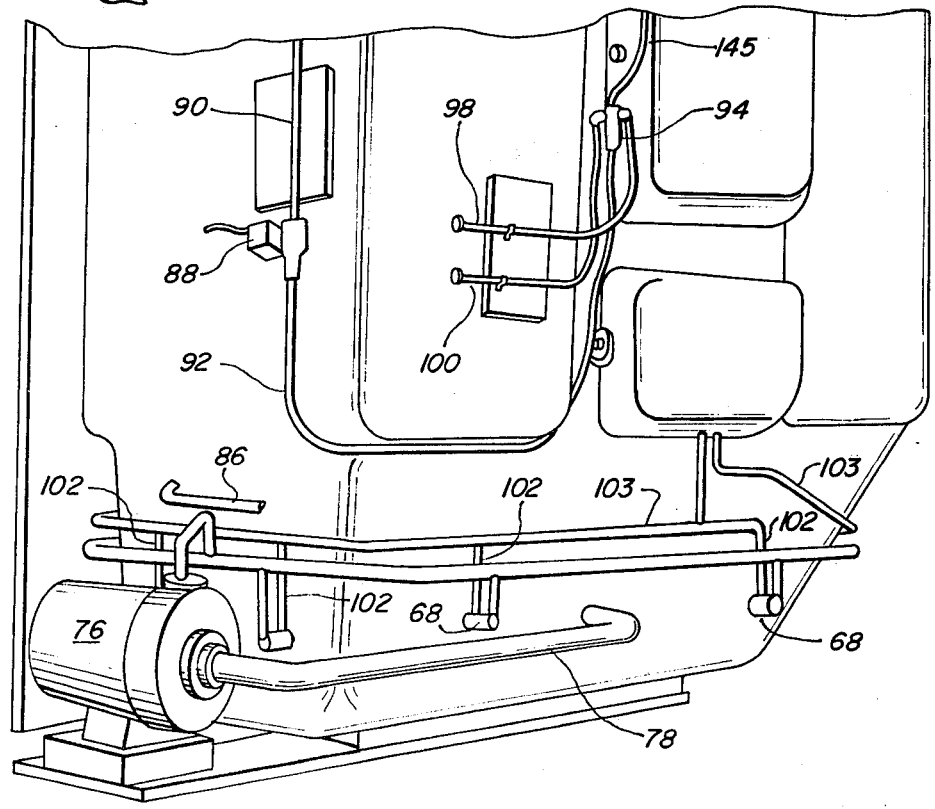
FIG. 5 is a perspective view showing the lower rear portion of the module of FIG. 1.

The delivery system for the mist mode includes a solenoid valve 88 (see FIG. 5) and water lines 90, 92. As shown line 90 runs from valve 80 to the mist heads 74 while line 92 runs from valve 88 to a mixing valve 94 (FIG. 5) which is controlled by the personal shower control 96 located in the recessed storage compartment 34, as will be described. Hot and cold water lines 98, 100 deliver water to the mixing valve 94.

Figure 7:
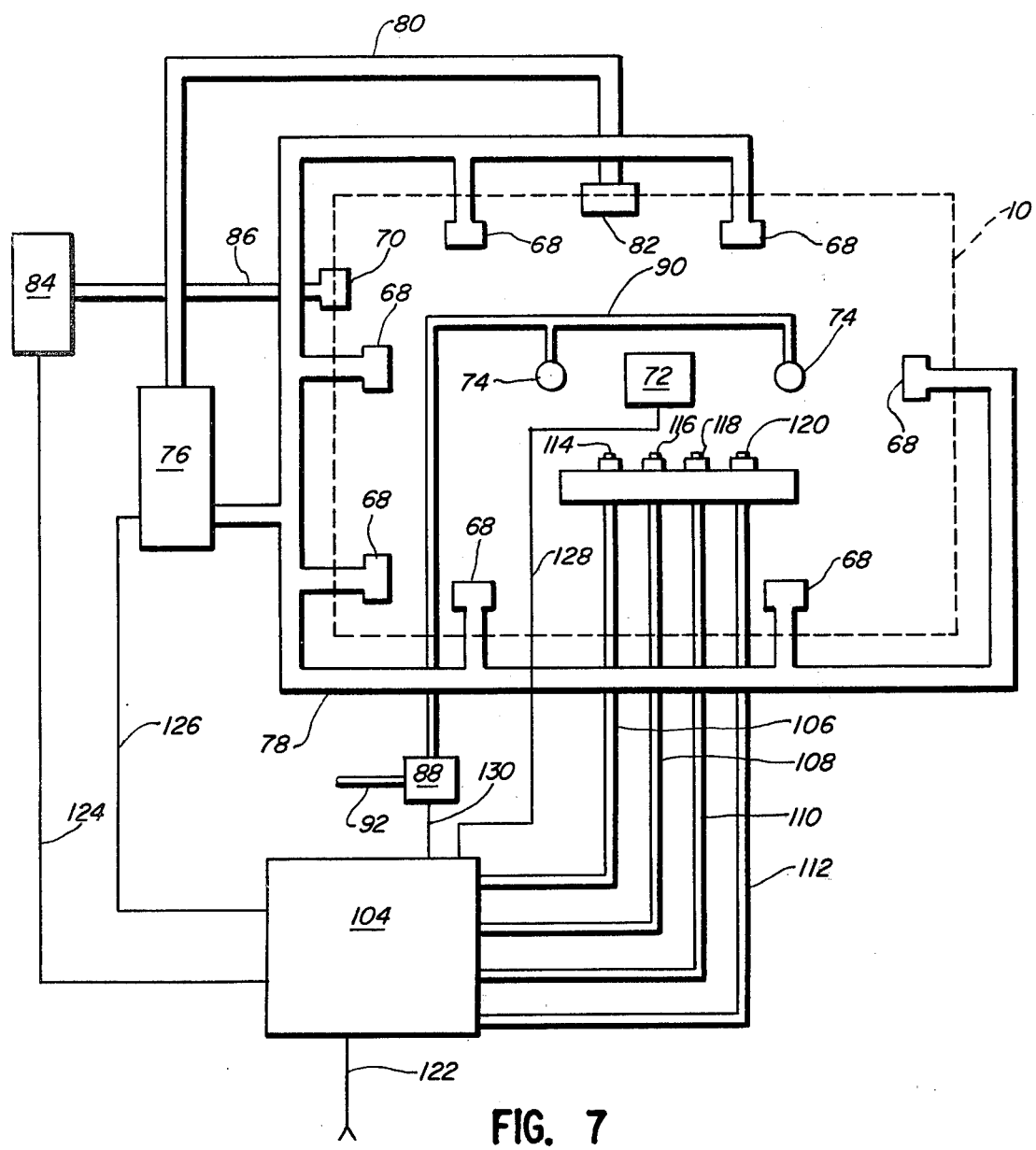
FIG. 7 is a simplified schematic of the delivery and operating systems for the module.

For the tanning mode, the delivery system simply comprises electrical power line 128 (shown in FIG. 7 only).

Figure 6:
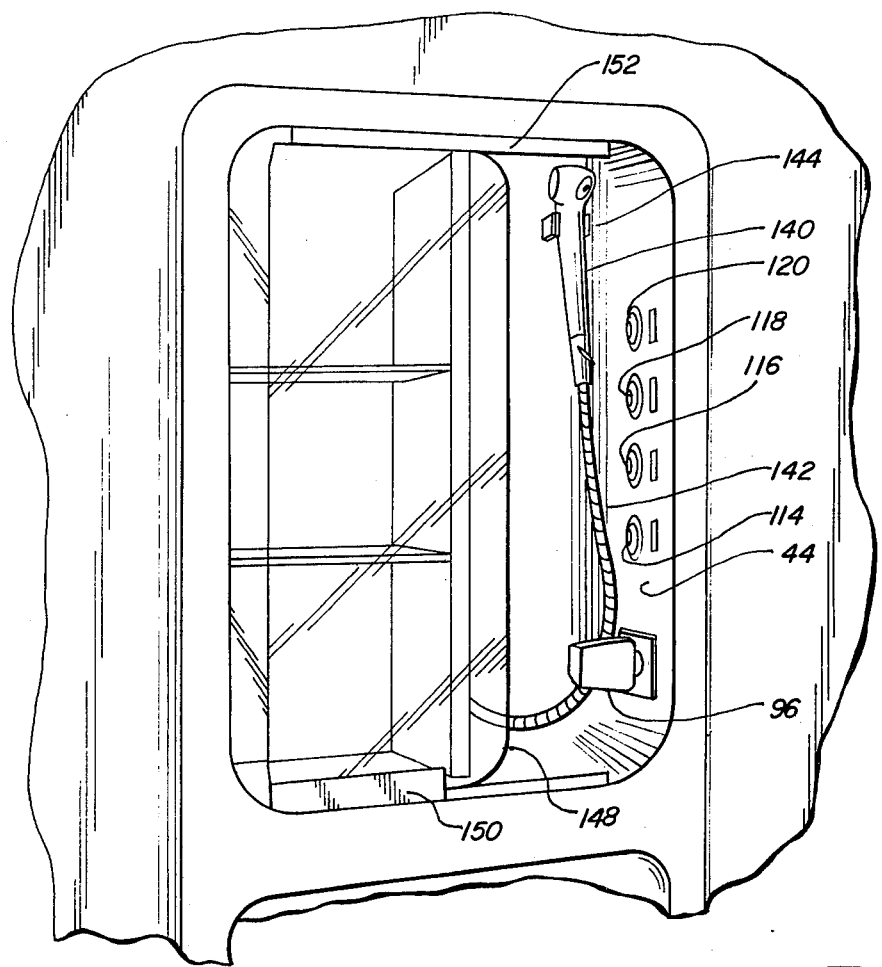
FIG. 6 is an enlarged fragmentary perspective view of the recessed storage compartment.

With reference to FIG. 7, the operating system for the whirlpool, steam, mist and tanning modes comprises an electro-pneumatic switch unit 104 which responds to pneumatic control signals received from pneumatic control lines 106, 108, 110 and 112. The control lines 106, 108, 110 and 112 are respectively connected to control push buttons 114, 116, 118 and 120, respectively which are mounted in the recessed storage compartment 34 as best shown in FIG. 6. In the presently preferred embodiment the switch unit 104 incorporates four air switches, each being connected to a separate one of the lines 106–112 which comprise flexible air hoses. When any of the control push buttons is depressed, a control signal in the form of a burst of air is forced through the corresponding hose to the corresponding air switch to turn the same either "on" or "off" depending upon the state of the switch. The air switches are of conventional design and readily available, as are the push button controls.

The four air switches of unit 104 are connected to switch power from a common input power line 122 to four output power lines 124, 126, 128 and 130 respectively connected to drive the steam generator 84, the pump 76, the ultraviolet lamp 72 and the solenoid valve 88. In the preferred arrangement the air switches include timing circuits, programmed to provide a 10 minute cycle for each of the modes. If the user does not wish to continue a mode for a full 10 minute span, the mode can be terminated by turning the air switch "off" by depressing the corresponding control push button.

The presently preferred embodiment imcorporates a pair of control valves 132, 134 located along the bottom wall 52 of the recessed grab bar compartment 36. The operation of such valves is well known and therefore will be only briefly discussed. In this regard, the whirlpool jet nozzles 68 have air inlets 102 associated therewith from which air is drawn into the discharging jet stream of water (to form bubbles). The air inlets are connected via piping to the valves 132, 134. The valves operate to control the amount of air which can be drawn into the jet streams (via venturi effect) by opening and closing the piping to the atmosphere.

For added convenience and safety, shelves 136 are mounted in recessed storage compartment 34 which extend less than the full length thereof. A divider 138 separates the shelves from the remainder of the compartment and defines an area for locating a conventional hand held shower consisting of a shower head 140 and flexible hose 142. A hanger 144 is provided in the compartment for hanging the shower head 140. The hose 142 is connected via a water line 145 to valve 94. In order to prevent substantial discharge of water through head 140 during the mist mode, head 140 includes a turn off cock.

The recessed storage compartment 34 can be closed via sliding doors 146, 148 mounted on tracks 150, 152 disposed along the upper and lower wall portions 40, 42.

As best shown in FIG. 3, the bottom wall 52 of recessed grab bar compartment 36 and the bottom of the flared portion 16F serves as a seat on which a removable bench unit 154 may be rested.

As will be obvious to one skilled in the art, many modifications, variations, alterations and the like may be made in the practices of the present invention without departing from the spirit and scope thereof as set forth in the preceding description and in the claims which follow.

What is claimed is:

1. A multi-mode bath module having an enclosed interior comprising spaced-apart top and bottom walls with opposed pairs of side and end walls extending generally vertically therebetween to jointly therewith define the interior of the module, said walls being joined integrally to define a monolithic shell-like structure, one of said side walls having a relatively large opening therethrough for providing access to said interior, first door means for opening and closing said access, the other of said side walls having a first recessed portion defining a storage compartment, second door means slidably mounted in substantially coplanar relation to said other of said side walls for opening and closing said first recessed portion, said walls having relatively small openings therein, a plurality of comfort mode determining means communicating with the interior of said module through said openings, operating means connected to said mode determining means and responsive to pneumatic control signals for controlling operation of said mode determining means, control means mounted in said recessed portion for producing said control signals, a hand held shower having a shower head and a flexible water hose, a water input for said hose mounted in said first recessed portion, means for removably supporting said shower head in said first recessed portion, and valve means mounted in said first recessed portion for controlling the temperature of water dispensed through said shower head.

2. A module in accordance with the claim 1 wherein said control means comprise a plurality of push buttons.

3. A module in accordance with claim 1 wherein said side and end walls include upper and lower portions, said lower portions together with said bottom wall defining a bathtub, said relatively large opening and said first recessed portion being located in the upper portions of said side walls.

4. A module in accordance with claim 3 wherein said other of said side walls further includes a second recessed portion located above said lower portions and below said first recessed portion, and means defining a grab bar mounted in said second recessed portion.

5. A module in accordance with claim 1 and further including a plurality of shelves mounted in said first recessed portion.

6. A module in accordance with claim 1 wherein one of said mode determining means comprises steam producing means, said operating means including means responsive to a first pneumatic signal for enabling operation of said steam producing means for a predetermined length of time and responsive to a second pneumatic signal occurring prior to said length of time for disabling operation of said steam producing means.

* * * * *